(12) United States Patent
Sakata et al.

(10) Patent No.: US 12,179,168 B2
(45) Date of Patent: Dec. 31, 2024

(54) PHOTORESPONSIVE OXYGEN STORAGE MATERIAL

(71) Applicant: Panasonic Intellectual Property Management Co., Ltd., Osaka (JP)

(72) Inventors: Naoya Sakata, Hyogo (JP); Masashi Morita, Tokyo (JP); Hidekazu Arase, Hyogo (JP); Ryotaro Matsuda, Aichi (JP); Akihiro Hori, Aichi (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 794 days.

(21) Appl. No.: 17/361,377

(22) Filed: Jun. 29, 2021

(65) Prior Publication Data

US 2021/0322948 A1 Oct. 21, 2021

Related U.S. Application Data

(63) Continuation of application No. PCT/JP2019/048204, filed on Dec. 10, 2019.

(30) Foreign Application Priority Data

Feb. 4, 2019 (JP) .................................. 2019-017997

(51) Int. Cl.
*B01J 20/02* (2006.01)
*B01J 20/34* (2006.01)
*C01B 13/02* (2006.01)

(52) U.S. Cl.
CPC ........... *B01J 20/0211* (2013.01); *B01J 20/34* (2013.01); *C01B 13/02* (2013.01)

(58) Field of Classification Search
CPC ....... B01D 53/04; B01J 20/0211; B01J 20/22; B01J 20/34; C01B 13/02; C01B 13/0262; C07D 487/22; C07F 11/00
See application file for complete search history.

(56) References Cited

U.S. PATENT DOCUMENTS

2014/0107333 A1\* 4/2014 Ma ....................... C07D 487/22
540/145

FOREIGN PATENT DOCUMENTS

| JP | 2000-070650 | | 3/2000 |
| JP | 2000070651 A | \* | 3/2000 |

(Continued)

OTHER PUBLICATIONS

Morris et al. Inorg. Chem. 2012, 51, 6443-6445 (Year: 2012).\*

(Continued)

*Primary Examiner* — Samir Shah
*Assistant Examiner* — Jordan W Taylor
(74) *Attorney, Agent, or Firm* — Rimon P.C.

(57) ABSTRACT

A photoresponsive oxygen storage material includes a plurality of unit cells. Each of the plurality of unit cells has a shape of a cube having eight corners and six faces. Each of the plurality of unit cells includes a plurality of zirconium-oxo clusters each located at a corresponding corner of the eight corners, and a plurality of ligands each located on a corresponding face of the six faces and each having a porphyrin skeleton and including greater than or equal to 1 and less than or equal to 4 carboxy groups. A molybdenum ion is located at a center of the porphyrin skeleton, and at least some of the plurality of unit cells are empty.

14 Claims, 8 Drawing Sheets

(56) References Cited

FOREIGN PATENT DOCUMENTS

JP          2007-516221        6/2007
WO          2004/101575       11/2004

OTHER PUBLICATIONS

Srivastava et al. J. Am. Chem. Soc. 1970, 92, 5518 (Year: 1970).*
Kuroki et al. JP2000070651A English Translation (Year: 2000).*
Neves et al. Microporous and Mesoporous Materials 2015, 202, 106-114 (Year: 2015).*
English Translation of Chinese Search Report dated Dec. 11, 2023 for the related Chinese Patent Application No. 201980040786.0.
William Morris et al, "Synthesis, Structure, and Metalation of Two New Highly Porous Zirconium Metal-Organic Frameworks", «Return to Issueprevcommunicationnext » vol. 51, Issue 12, pp. 6443-6445.
International Search Report of PCT application No. PCT/JP2019/048204 dated Feb. 4, 2020.
Leslie J. Murray et al., "Highly-Selective and Reversible O2 Binding in Cr3(1,3,5-benzenetricarboxylate)2", Journal of the American Chemical Society, May 19, 2010, 132, 7856-7857.
Eric D. Bloch et al., "Selective Binding of O2 over N2 in a Redox-Active Metal-Organic Framework with Open Iron(II) Coordination Sites", Journal of the American Chemical Society, Aug. 10, 2011, 133, 14814-14822.
Konstantin Epp et al., "Dual Site Lewis-Acid Metal-Organic Framework Catalysts for CO2 Fixation: Counteracting Effects of Node Connectivity, Defects and Linker Metalation", ChemCatChem 2018, 10, Jul. 4, 2018, 3506-3512.

* cited by examiner

PHOTORESPONSIVE OXYGEN STORAGE MATERIAL

BACKGROUND

1. Technical Field

The present disclosure relates to a photoresponsive oxygen storage material.

2. Description of the Related Art

Metal-organic frameworks are one of porous materials that can store gas. Metal-organic frameworks are constituted by metal ions (or metal clusters) and organic ligands. In metal-organic frameworks, a coordinate bond is formed between an organic ligand and a metal ion (or a metal cluster).

Unlike an existing porous material such as activated carbon or zeolite, as disclosed in Japanese Patent No. 4937749, the pore size and the specific surface area of a metal-organic framework can be changed by appropriately selecting a metal ion (or a metal cluster) and an organic ligand. As disclosed in Leslie J. Murray et. al., "Highly-Selective and Reversible $O_2$ Binding in $Cr_3(1,3,5$-benzene-tricarboxylate$)_2$", Journal of the American Chemical Society, 2010, 132, 7856-7857 and Eric D. Bloch et. al., "Selective Binding of $O_2$ over $N_2$ in a Redox Active Metal Organic Framework with Open Iron(II) Coordination Sites", Journal of the American Chemical Society, 2011, 133, 14814-14822, in methods for storing oxygen by using a metal-organic framework, the amount of oxygen adsorbed is improved by using coordinatively unsaturated sites of metal ions of Cr or Fe.

Japanese Unexamined Patent Application Publication No. 2000-70650 discloses that oxygen is adsorbed by a porphyrin containing an oxomolybdenum ion, the porphyrin being dispersed in mesoporous silica, and that the oxygen is released by irradiating, with light, the porphyrin to which the oxygen has been adsorbed in this manner.

SUMMARY

In one general aspect, the techniques disclosed here feature a photoresponsive oxygen storage material including a plurality of unit cells. Each of the plurality of unit cells has a shape of a cube having eight corners and six faces. Each of the plurality of unit cells includes a plurality of zirconium-oxo clusters each located at a corresponding corner of the eight corners, and a plurality of ligands each located on a corresponding face of the six faces and each having a porphyrin skeleton and including greater than or equal to 1 and less than or equal to 4 carboxy groups. A molybdenum ion is located at a center of the porphyrin skeleton, and at least some of the plurality of unit cells are empty.

It should be noted that general or specific embodiments may be implemented as a system, a method, an integrated circuit, a computer program, a storage medium, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

DETAILED DESCRIPTION

Embodiments of the present disclosure will be described in detail below with reference to the drawings.

First Embodiment

Figure 1A:
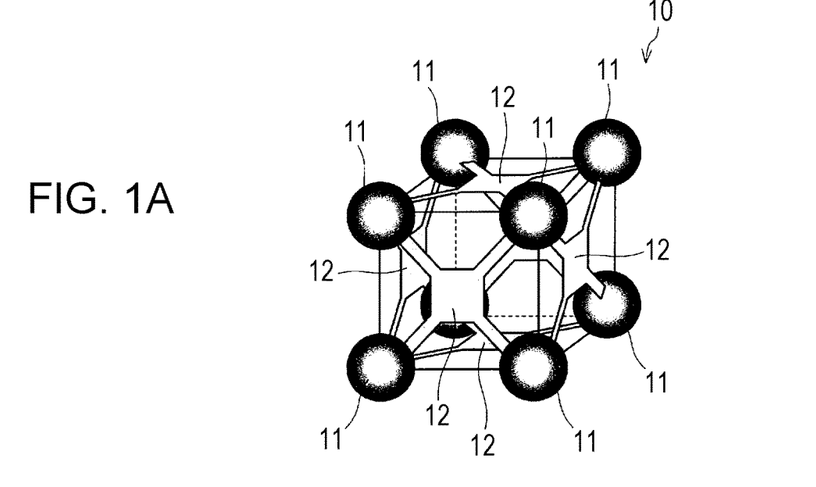
FIG. 1A is a schematic view of one unit cell included in a metal-organic framework forming a photoresponsive oxygen storage material according to a first embodiment.

FIG. 1A is a schematic view of a unit cell of a photoresponsive oxygen storage material (that is, a metal-organic framework) according to a first embodiment of the present disclosure. As illustrated in FIG. 1A, the photoresponsive oxygen storage material according to the first embodiment is formed of a metal-organic framework. The metal-organic framework includes a plurality of unit cells 10. Each of the plurality of unit cells 10 has a shape of a cube having eight corners and six faces. Each of the plurality of unit cells 10 includes a plurality of zirconium-oxo clusters 11 each located at a corresponding corner of the eight corners, and a plurality of ligands 12 each located on a corresponding face of the six faces and each having a porphyrin skeleton and including greater than or equal to 1 and less than or equal to 4 carboxy groups. A molybdenum ion is located at a center of the porphyrin skeleton. At least some of the plurality of unit cells is empty.

In the metal-organic framework according to the first embodiment, a coordinate bond is formed between a molybdenum ion and the ligand 12. In other words, the ligand 12 is a ligand in which a coordinate bond is formed between a molybdenum ion and the ligand 12.

Figure 1B:
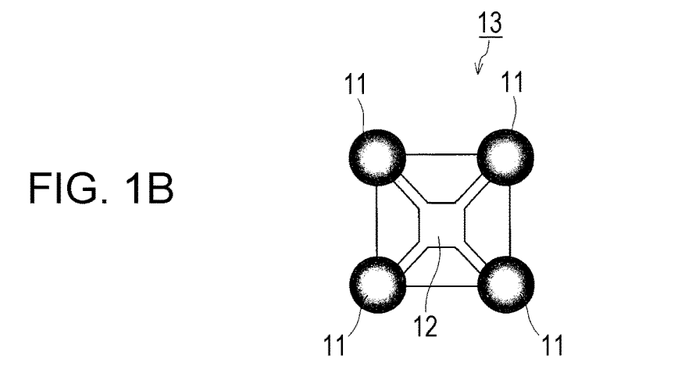
FIG. 1B is a schematic view of a two-dimensional structure of the unit cell of the metal-organic framework illustrated in FIG. 1A.

FIG. 1B is a schematic view of a two-dimensional unit structure 13 of the unit cell 10 of the metal-organic framework illustrated in FIG. 1A. The two-dimensional unit structure 13 is one face included in the six faces described above. In the two-dimensional unit structure 13, zirconium-oxo clusters 11 are crosslinked by a ligand 12. Crosslinking will be described later. The metal-organic framework has a three-dimensional structure (that is, a unit cell 10) including a plurality of two-dimensional unit structures 13.

Figure 1C:
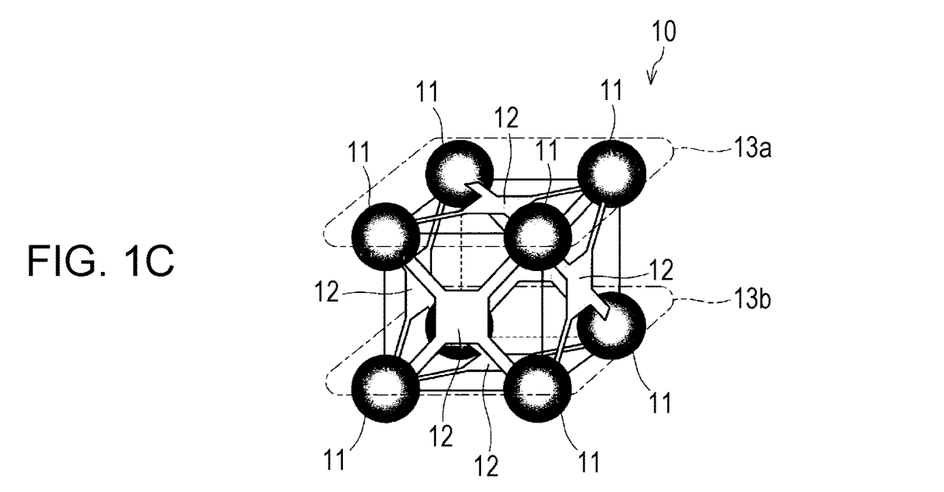
FIG. 1C is a schematic view of a three-dimensional structure of the metal-organic framework illustrated in FIG. 1A.

FIG. 1C is a schematic view of the three-dimensional structure (that is, the unit cell 10) of the metal-organic framework. As illustrated in FIG. 1C, the three-dimensional structure (that is, the unit cell 10) of the metal-organic framework includes a first two-dimensional unit structure 13a and a second two-dimensional unit structure 13b therein. The first two-dimensional unit structure 13a and the second two-dimensional unit structure 13b are parallel to each other. The first two-dimensional unit structure 13a and the second two-dimensional unit structure 13b are each constituted by four zirconium-oxo clusters 11 and one ligand 12. In each of the first two-dimensional unit structure 13a and the second two-dimensional unit structure 13b, the four zirconium-oxo clusters 11 are crosslinked by the ligand 12.

The metal-organic framework according to the first embodiment has an oxygen adsorption capacity. In other words, oxygen molecules can selectively adsorb on the metal-organic framework according to the first embodiment. Furthermore, oxygen adsorbed on the metal-organic framework according to the first embodiment is released from the metal-organic framework according to the first embodiment by light.

Molybdenum Ion

The molybdenum ion having a coordinate bond formed between the molybdenum ion and the ligand may be a molybdenum ion that is not bound to oxygen. Alternatively, the molybdenum ion having a coordinate bond formed between the molybdenum ion and the ligand may be an oxomolybdenum ion. The oxomolybdenum ion is represented by chemical formula $[Mo=O]^{2+}$. An example of the molybdenum ion is a tetravalent oxomolybdenum ion.

Zirconium-Oxo Cluster 11

An example of each of the zirconium-oxo clusters is $Zr_6(OH)_4O_4$, $Zr_6O_4(OH)_{10}$, $Zr_6(H_2O)_8O_8$, or $Zr_6(OH)_8O_4$. The zirconium-oxo clusters 11 are each preferably $Zr_6(OH)_4O_4$.

Ligand 12

The ligand 12 has a porphyrin skeleton and includes greater than or equal to 1 and less than or equal to 4 carboxy groups. The term "1 to 4" used in the present specification means greater than or equal to 1 and less than or equal to 4. In other words, the term "1 to 4" means a number greater than or equal to 1 and less than or equal to 4 (inclusive).

The ligand 12 is preferably a porphyrin including 4 carboxy groups. The ligand 12 is more preferably tetracarboxyphenyl porphyrin (hereinafter referred to as "TCPP") represented by formula (1) below. Formula (1) below shows TCPP that forms a coordinate bond with an oxomolybdenum ion represented by chemical formula $[Mo=O]^{2+}$.

(1)

In formula (1), M represents Mo=O.

A porphyrin having 2 carboxy groups can form a two-dimensional structure and a three-dimensional structure with zirconium-oxo clusters. A porphyrin having 1 or 3 carboxy groups is mixed with a porphyrin having 2 or 4 carboxy groups and can form a two-dimensional structure and a three-dimensional structure with zirconium-oxo clusters. Accordingly, the ligand 12 is not limited to a porphyrin including 4 carboxy groups. In other words, the ligand 12 may be a porphyrin including 1, 2, or 3 carboxy groups.

Production Method

The metal-organic framework according to the first embodiment can be produce by, for example, the following method.

First, a metal-organic framework constituted by zirconium-oxo clusters 11 and ligands 12 each having a porphyrin skeleton and including greater than or equal to 1 and less than or equal to 4 carboxy groups is synthesized. In the synthesis, a solution in which a zirconium compound and a porphyrin material are mixed is prepared. Needless to say, the zirconium compound and the porphyrin material are used as a zirconium source and a ligand, respectively. Subsequently, the solution is heated to a predetermined temperature. The zirconium compound is caused to react with the ligand (that is, the porphyrin material) by the heating. Thus, a metal-organic compound is obtained.

Furthermore, a molybdenum ion is introduced into the metal-organic compound obtained as described above. More specifically, a molybdenum source is added to the metal-organic compound and is then mixed. In this manner, the metal-organic compound reacts with the molybdenum source at a predetermined temperature to obtain a reaction product. The resulting reaction product is washed and then dried by heating under vacuum. Thus, the metal-organic framework according to the first embodiment can be obtained.

The photoresponsive oxygen storage material (that is, the metal-organic framework) according to the first embodiment can adsorb oxygen as described above. In other words, oxygen can adsorb on the photoresponsive oxygen storage material (that is, the metal-organic framework) according to the first embodiment.

A method for storing oxygen by using the photoresponsive oxygen storage material according to the first embodiment includes a step of bringing the photoresponsive oxygen storage material into contact with gas containing oxygen molecules. The oxygen molecules are trapped inside the photoresponsive oxygen storage material by the contact. Thus, the oxygen molecules are stored inside the unit cells 10.

In this method for storing oxygen, oxygen is selectively adsorbed from mixed gas onto the photoresponsive oxygen storage material at room temperature and stored. In an example, the photoresponsive oxygen storage material is brought into contact with gas containing oxygen molecules at room temperature (for example, 25 degrees Celsius).

Oxygen stored in the photoresponsive oxygen storage material is released (that is, desorbed) from the photoresponsive oxygen storage material by irradiating the photoresponsive oxygen storage material with light. In this manner, oxygen is quickly obtained at any timing by using the photoresponsive oxygen storage material. In an example, the photoresponsive oxygen storage material in which oxygen is stored is irradiated with the light at room temperature (for example, 25 degrees Celsius).

The amount of oxygen to be trapped in the photoresponsive oxygen storage material can be controlled by changing the pressure of oxygen in the gas containing oxygen molecules. Accordingly, the pressure of oxygen can be appropriately set in accordance with the amount of oxygen to be trapped.

Second Embodiment

An oxygen-adsorbing material including the photoresponsive oxygen storage material described in the first embodiment and an oxygen storage apparatus including the photoresponsive oxygen storage material described in the first embodiment will be described below.

The oxygen-adsorbing material according to a second embodiment includes the photoresponsive oxygen storage material described in the first embodiment. The oxygen-adsorbing material is a material that can trap oxygen molecules on a substance surface and may be a material that can trap oxygen molecules at room temperature and normal pressure.

The oxygen storage apparatus according to the second embodiment includes a container and the photoresponsive oxygen storage material described in the first embodiment, the photoresponsive oxygen storage material being disposed in the container.

Figure 2:
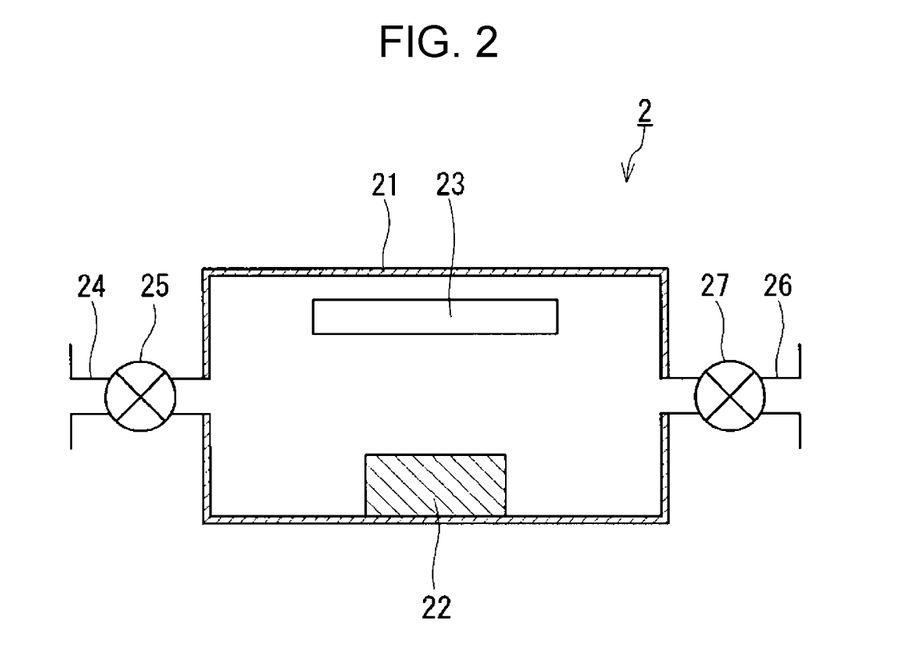
FIG. 2 is a schematic view of an oxygen storage apparatus according to a second embodiment.

FIG. 2 is a schematic view illustrating an example of the oxygen storage apparatus according to the second embodiment of the present disclosure. An oxygen storage apparatus 2 illustrated in FIG. 2 includes a container 21 and a photoresponsive oxygen storage material 22 disposed in the container 21. The oxygen storage apparatus 2 further includes a light irradiation device 23 disposed in the container 21. The container 21 includes a gas inlet 24 through which gas containing oxygen molecules is introduced into the container 21. The gas inlet 24 is provided with a valve 25. The container 21 further includes a gas outlet 26 through which oxygen molecules desorbed from the photoresponsive oxygen storage material 22 are led to the outside of the container 21. The gas outlet 26 is provided with a valve 27.

Gas containing oxygen molecules is supplied to the inside of the container 21 through the gas inlet 24. During supply of the gas, the valve 25 is opened. The photoresponsive oxygen storage material 22 is brought into contact with the gas in this manner. The oxygen molecules contained in the gas are absorbed by the photoresponsive oxygen storage material 22 and are thereby stored in the photoresponsive oxygen storage material 22. The pressure and the temperature of the gas during contact between the photoresponsive oxygen storage material 22 and the gas are not limited as long as oxygen molecules can be adsorbed on the photoresponsive oxygen storage material 22. The temperature may be, for example, room temperature (for example, 25° C.). The amount of oxygen adsorbed on the photoresponsive oxygen storage material 22 can be controlled by changing the pressure of oxygen. Accordingly, the pressure can be appropriately selected in accordance with a desired amount of oxygen stored.

When the photoresponsive oxygen storage material 22 is irradiated with light by using the light irradiation device 23, the oxygen molecules stored inside the photoresponsive oxygen storage material 22 are desorbed and released. The pressure and the temperature in the container 21 are not limited as long as oxygen molecules can be desorbed from the photoresponsive oxygen storage material 22. The temperature may be, for example, room temperature (for example, 25° C.). The amount of oxygen desorbed from the photoresponsive oxygen storage material 22 can be controlled by changing the pressure of oxygen. Accordingly, the pressure can be appropriately selected in accordance with a desired amount of oxygen desorbed. The oxygen molecules desorbed from the photoresponsive oxygen storage material 22 are released to the outside of the container 21 through the gas outlet 26. During release of the oxygen molecules, the valve 27 is opened.

The light applied to the photoresponsive oxygen storage material 22 may have a wavelength in the range of, for example, greater than or equal to 300 nm and less than or equal to 480 nm. The irradiation time is, for example, greater than or equal to 10 seconds and less than or equal to 1,000 seconds.

The oxygen storage apparatus according to the second embodiment may be any oxygen storage apparatus as long as the photoresponsive oxygen storage material is disposed in the container. Accordingly, an oxygen-adsorbing material including the photoresponsive oxygen storage material may be disposed in the oxygen storage apparatus 2 instead of the photoresponsive oxygen storage material 22.

The oxygen storage apparatus according to the second embodiment can store oxygen by causing oxygen to be effectively adsorbed on the photoresponsive oxygen storage material at room temperature and can easily desorb the oxygen by light irradiation. That is, the oxygen storage apparatus according to the second embodiment can selectively store oxygen from a mixed gas component at room temperature and can desorb the stored oxygen with a relatively low energy.

EXAMPLES

The present disclosure will be more specifically described below with reference to Examples below.
Preparation of Metal-Organic Framework Example 1

In Example 1, the following metal-organic framework 1 was synthesized.

Zirconium-Oxo Cluster 11: $Zr_6(OH)_4O_4$

Ligand 12: Tetracarboxyphenyl porphyrin containing oxomolybdenum ion

In the ligand 12, a coordinate bond was formed between the oxomolybdenum ion and tetracarboxyphenyl porphyrin.

In Example 1, the metal-organic framework 1 was synthesized by the following method. Tetracarboxyphenyl porphyrin (that is, TCPP, 0.05 grams, manufactured by Tokyo Chemical Industry Co., Ltd.), zirconium chloride oxide (0.25 grams, manufactured by FUJIFILM Wako Pure Chemical Corporation), and N,N-dimethylformamide (20 milliliters, manufactured by FUJIFILM Wako Pure Chemical Corporation, hereinafter referred to as "DMF") were mixed to prepare a raw material solution. Zirconium chloride oxide was used as a zirconium source.

The raw material solution was put in a vial tube (volume: 30 milliliters) and allowed to stand at 65 degrees Celsius for seven days. In this manner, TCPP was caused to react with zirconium chloride oxide to prepare a reaction product formed from a metal-organic compound.

The resulting reaction product was separated by centrifugal separation.

The separated solid was transferred to a Schlenk tube. Subsequently, molybdenumhexacarbonyl (1.5 grams, manufactured by Sigma-Aldrich Co. LLC) and decahydronaphthalene (100 milliliters, manufactured by FUJIFILM Wako Pure Chemical Corporation) were added to the Schlenk tube and mixed. Molybdenumhexacarbonyl was used as a molybdenum source. Thus, a mixture was prepared.

Subsequently, the mixture was allowed to stand at 190 degrees Celsius for six hours. In this manner, the metal-organic compound was caused to react with molybdenumhexacarbonyl to obtain a reaction product.

The resulting reaction product was separated by centrifugal separation.

The separated solid was washed with decahydronaphthalene, hexane, and dichloromethane three times and then dried by heating at 200 degrees Celsius under vacuum. Thus, a metal-organic framework in Example 1 was obtained.

Comparative Example 1

In Comparative Example 1, a metal-organic framework was obtained as in Example 1 except that the metal-organic framework did not include molybdenum ions. In other words, the metal-organic framework in Comparative Example 1 was the metal-organic compound in Example 1.

More specifically, the metal-organic compound obtained in Example 1 was washed with decahydronaphthalene, hexane, and dichloromethane three times and then dried by heating at 150 degrees Celsius under vacuum. Thus, a metal-organic framework in Comparative Example 1 was obtained.

Needless to say, unlike Example 1, molybdenumhexacarbonyl was not used in Comparative Example 1.

Comparative Example 2

In Comparative Example 2, a metal-organic framework was obtained as in Example 1 except that the metal-organic framework included magnesium ions instead of molybdenum ions.

More specifically, a metal-organic framework was synthesized as in Example 1 except for two matters (1) and (2) described below.

(1) Magnesium nitrate (0.16 grams, manufactured by FUJIFILM Wako Pure Chemical Corporation) and DMF (20 milliliters, manufactured by FUJIFILM Wako Pure Chemical Corporation) were used instead of molybdenumhexacarbonyl and decahydronaphthalene, respectively. Needless to say, magnesium nitrate was used as a magnesium source.

(2) The metal-organic framework in Comparative Example 2 was washed with DMF and dichloromethane and then dried by heating at 150 degrees Celsius instead of washing the metal-organic framework with decahydronaphthalene, hexane, and dichloromethane followed by drying by heating at 200 degrees Celsius.

Structural Analysis

Figure 3A:
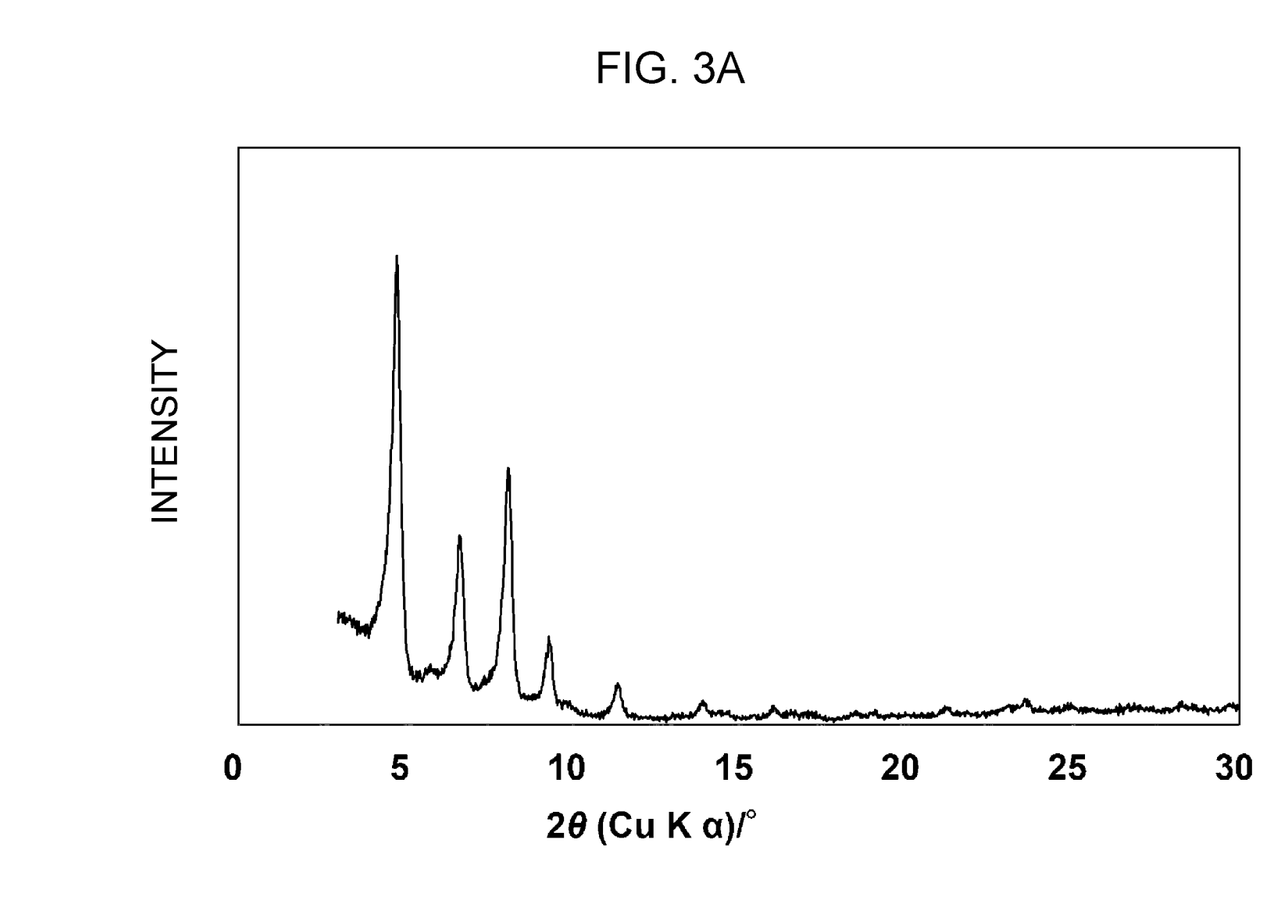
FIG. 3A shows an X-ray diffraction pattern of a metal-organic framework actually synthesized in Example 1.
Figure 3B:
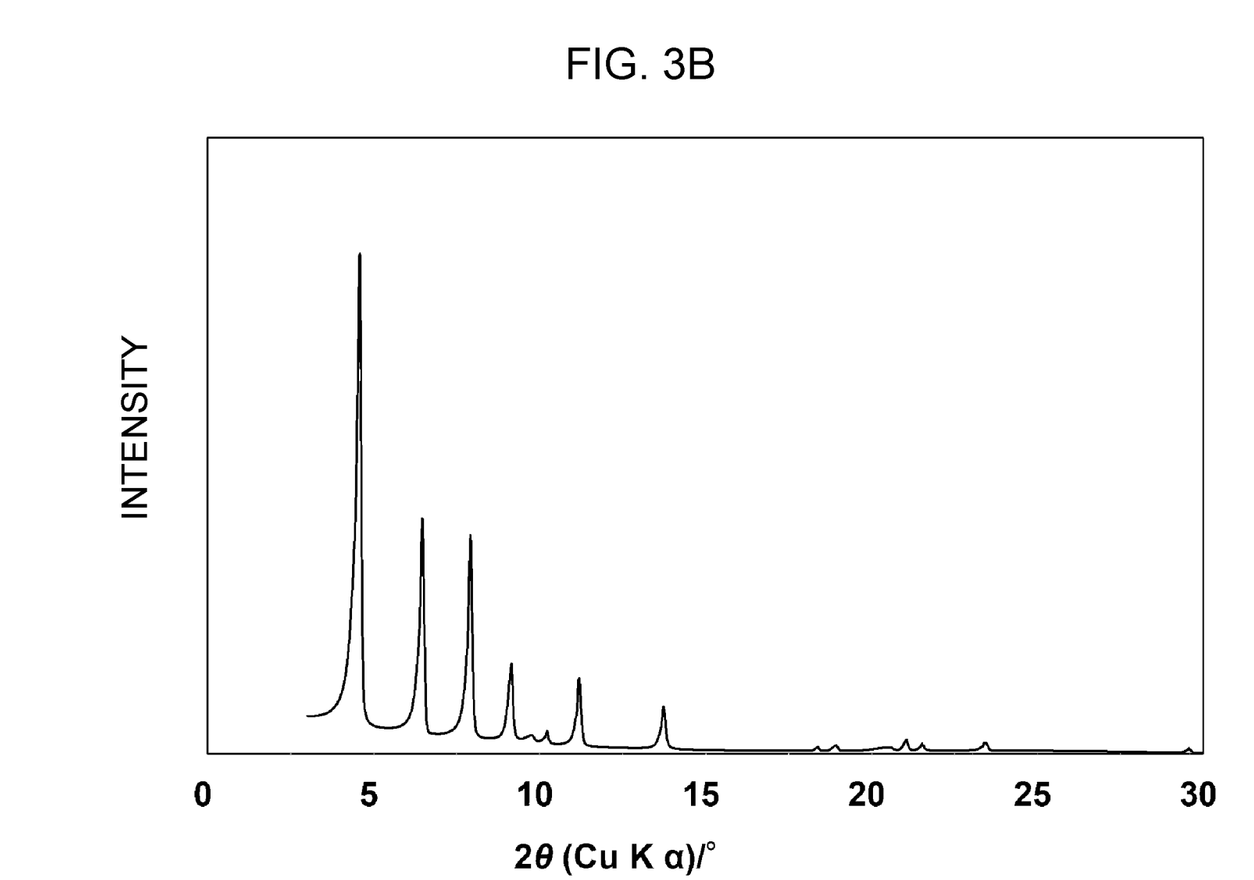
FIG. 3B shows an X-ray diffraction pattern of a metal-organic framework actually synthesized in Comparative Example 1.
Figure 3C:
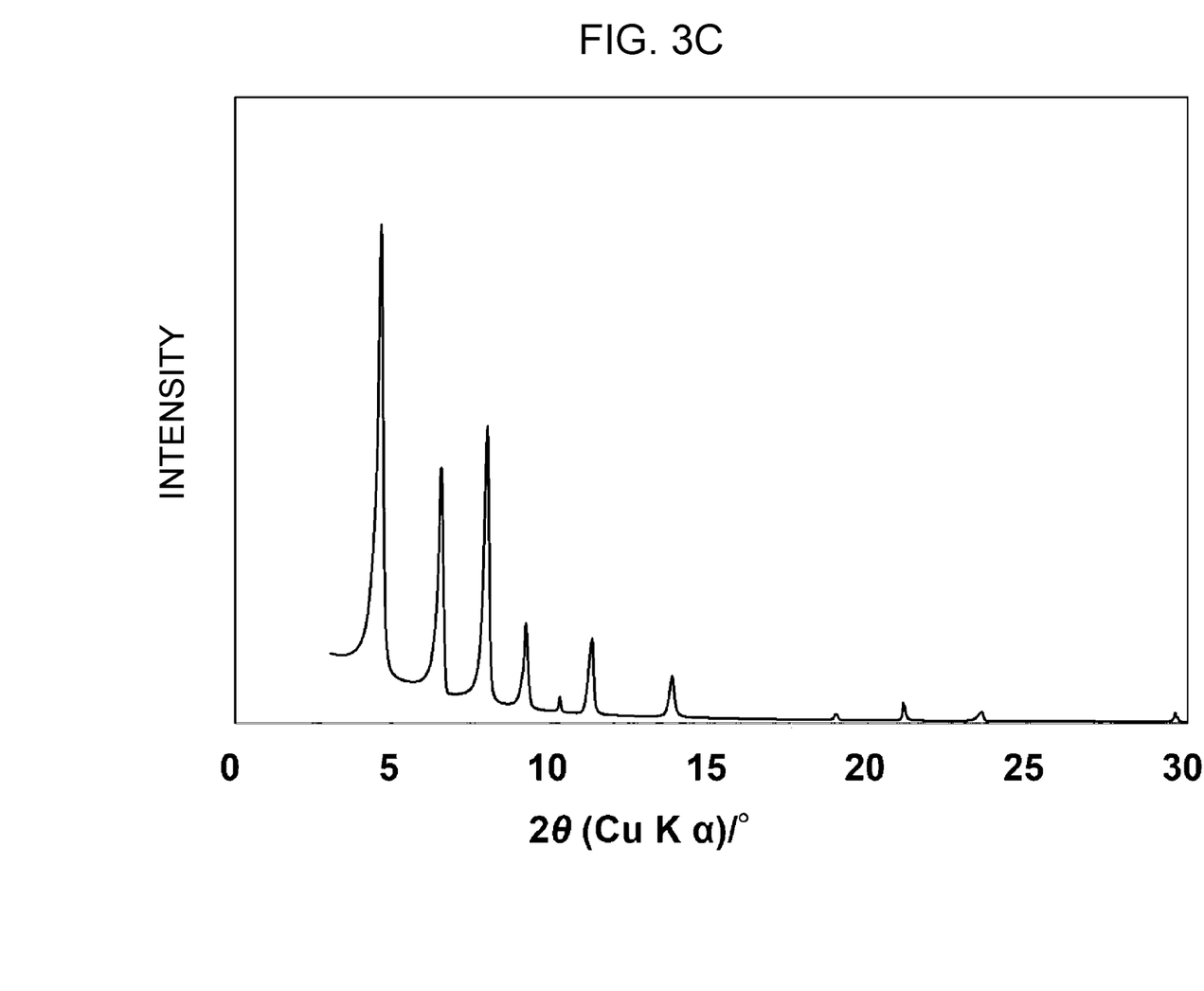
FIG. 3C shows an X-ray diffraction pattern of a metal-organic framework actually synthesized in Comparative Example 2.
Figure 3D:
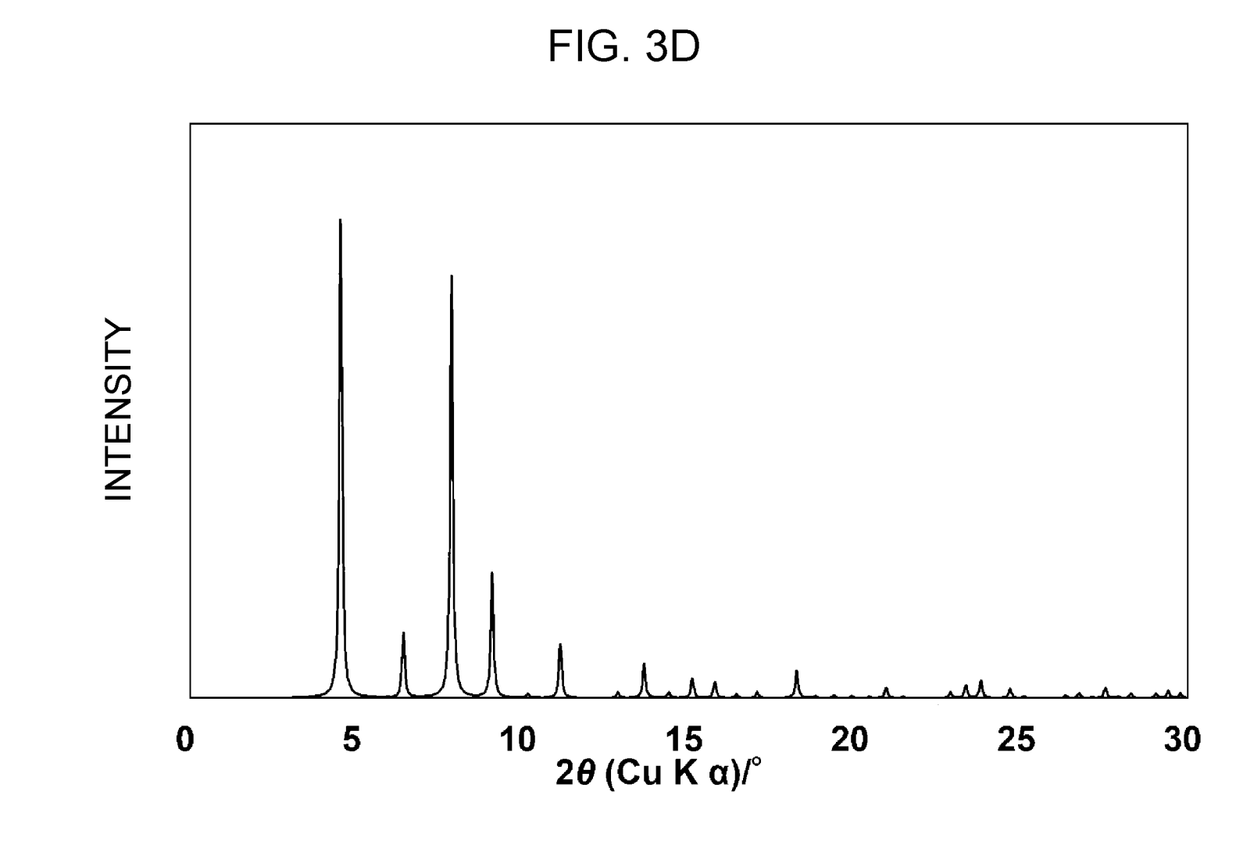
FIG. 3D shows an X-ray diffraction pattern of a metal-organic framework simulated in Example.

The metal-organic frameworks in Example 1, Comparative Example 1, and Comparative Example 2 were subjected to X-ray diffractometry. FIGS. 3A to 3C show X-ray diffraction patterns of the metal-organic frameworks in Example 1, Comparative Example 1, and Comparative Example 2, respectively. FIG. 3D is a chart showing an X-ray diffraction pattern simulated on the basis of the crystal structure of a metal-organic framework. Details of the simulation will be described in detail at the end of the present specification.

The X-ray diffraction patterns of the metal-organic frameworks in Example 1, Comparative Example 1, and Comparative Example 2 were identical to the X-ray diffraction pattern simulated from the crystal structure. Thus, the inventors of the present invention confirmed that the metal-organic frameworks in Example 1, Comparative Example 1, and Comparative Example 2 were metal-organic frameworks constituted by zirconium-oxo clusters and porphyrins. The inventors further confirmed that molybdenum and magnesium were contained in the metal-organic frameworks in Example 1 and Comparative Example 2, respectively, by inductively coupled plasma spectroscopy (hereinafter referred to as "ICP spectroscopy").

Oxygen Adsorption Capacity

An oxygen adsorption capacity of the metal-organic framework in Example 1 was measured as described below.

Figure 4:
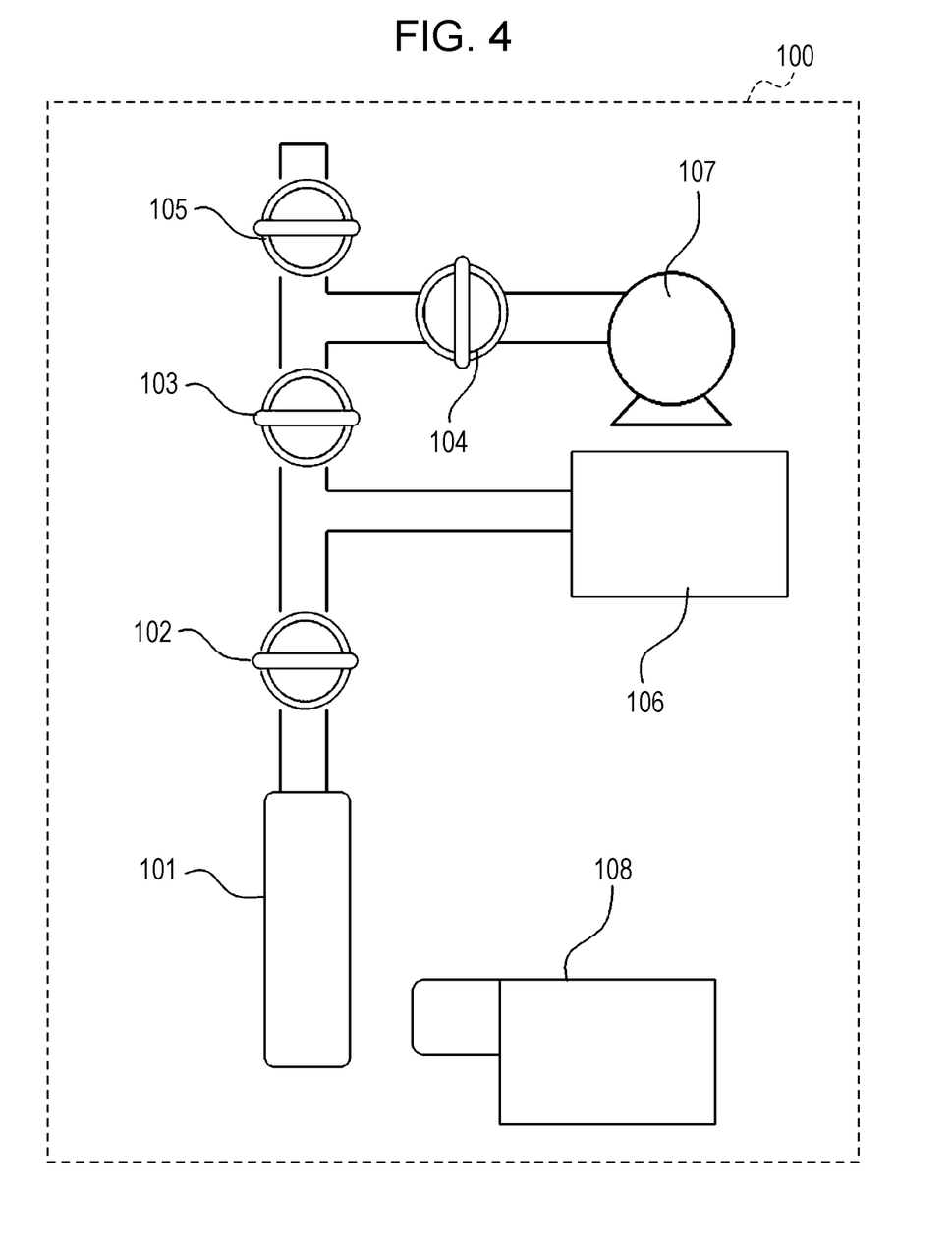
FIG. 4 is a schematic view of a measuring apparatus used in Example 1.

FIG. 4 is a schematic view of a measuring apparatus 100 used in Example. The measuring apparatus 100 included a sample tube 101, a first valve 102, a second valve 103, a third valve 104, a fourth valve 105, a pressure gauge 106, a vacuum pump 107, and a lamp 108. The lamp 108 was a high-pressure mercury lamp (manufactured by USHIO INC., trade name "Optical Modulex").

First, the metal-organic framework (5.4 milligrams) in Example 1 was placed in the sample tube 101. The first valve 102, the second valve 103, and the third valve 104 were opened, and the fourth valve 105 was closed. Subsequently, the inside of the measuring apparatus 100 was evacuated by using the vacuum pump 107. While the inside of the measuring apparatus 100 was evacuated, the metal-organic framework in Example 1 was heated at 200 degrees Celsius for 12 hours to remove gas contained in the metal-organic framework in Example 1. It is publicly known that gas absorbed by a metal-organic framework is desorbed by heating the metal-organic framework. After heating, the third valve 104 was closed.

Next, the fourth valve 105 was opened to supply oxygen gas to the measuring apparatus 100. When the pressure of oxygen gas in the measuring apparatus 100 reached 100 kPa, the fourth valve 105 was closed. Thus, oxygen gas was stored inside the metal-organic framework in Example 1.

The third valve 104 was opened. Subsequently, the pressure of the inside of the measuring apparatus 100 was reduced by using the vacuum pump 107 until the pressure of the gas in the measuring apparatus 100 reached 0.2 kPa. After pressure reduction, the second valve 103 was closed.

Next, the metal-organic framework in Example 1 was irradiated with light for one minute by using the lamp 108. The light had a wavelength of 370 nanometers and an intensity of 122 mW/cm$^2$. After irradiation, the pressure of the gas in the measuring apparatus 100 increased to 0.68 kPa.

Needless to say, the increase in the pressure of the gas in the measuring apparatus 100 means that oxygen gas (that is, oxygen molecules) stored in the metal-organic framework in Example 1 was desorbed and released by irradiating the metal-organic framework in Example 1 with light.

The photoresponsive oxygen storage material according to the present disclosure can trap oxygen molecules inside the photoresponsive oxygen storage material by being brought into contact with gas containing oxygen molecules and can desorb the oxygen molecules trapped in the photoresponsive oxygen storage material by irradiating the photoresponsive oxygen storage material with light. Accordingly, the photoresponsive oxygen storage material according to the present disclosure is suitable for use in, for example, an oxygen-adsorbing material and an oxygen storage apparatus.

Details of Simulation of X-Ray Diffraction Pattern

Figure 3E:
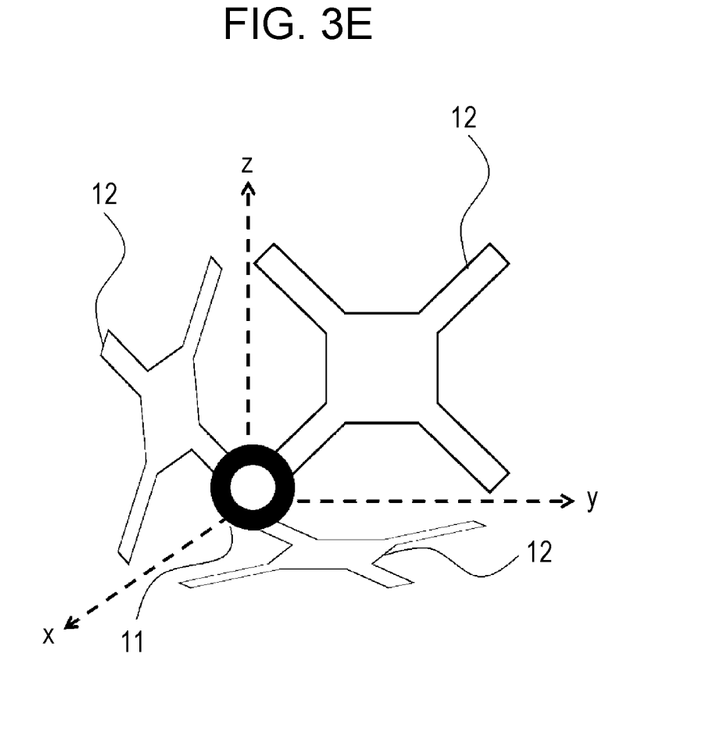
FIG. 3E is a schematic view of one repeating unit included in a metal-organic framework 1 used for a simulation in Example.

FIG. 3E is a schematic view of one repeating unit included in the metal-organic framework 1 used for the simulation in Example. In the metal-organic framework 1 used for the simulation in Example, a plurality of the repeating units were arranged along the X-axis, the Y-axis, and Z-axis included in FIG. 3E. The one repeating unit illustrated in FIG. 3E included one zirconium-oxo cluster 11 and three ligands 12. The one zirconium-oxo cluster 11 was constituted by $Zr_6(OH)_4O_4$. Accordingly, the one zirconium-oxo cluster 11 contained six Zr atoms. The ligands 12 were each tetracarboxyphenyl porphyrin including an oxomolybdenum ion represented by chemical formula $[Mo=O]^{2+}$. Accordingly, the three ligands 12 included three Mo atoms. The one repeating unit illustrated in FIG. 3E included 272 atoms.

In Example, an X-ray diffraction pattern obtained by irradiating a metal-organic framework in which the repeating unit illustrated in FIG. 3E was repeatedly arranged along the X-axis, the Y-axis, and Z-axis with X-rays (wavelength: 0.15418 nanometers) was simulated by using computer software (provided by Dassault Systemes, trade name: Materials Studio 2018 BIOVIA) for predicting powder X-ray diffraction peaks. As a result of this simulation, the X-ray diffraction pattern shown in FIG. 3D was obtained.

Coordinates of Atoms in Simulation in Example

| | | | | |
|---|---|---|---|---|
| Zr1 | Zr | 0.00540 | 0.10837 | −0.00962 |
| Zr2 | Zr | 0.00542 | 0.87271 | −0.01362 |
| Zr3 | Zr | 0.00361 | −0.01141 | 0.10650 |
| Zr4 | Zr | 0.00653 | −0.00776 | 0.87082 |
| Zr5 | Zr | 0.12309 | −0.00931 | −0.00996 |
| Zr6 | Zr | 0.88750 | −0.00906 | −0.01292 |
| O7 | O | 0.06705 | 0.05216 | 0.05300 |
| O8 | O | 0.94174 | 0.92682 | 0.04924 |
| O9 | O | 0.94319 | 0.05459 | 0.92595 |
| O10 | O | 0.06888 | 0.92891 | 0.92566 |
| O11 | O | 0.06873 | 0.05422 | 0.92743 |
| O12 | O | 0.94301 | 0.92876 | 0.92385 |
| O13 | O | 0.06718 | 0.92689 | 0.05105 |
| O14 | O | 0.94175 | 0.05255 | 0.05169 |
| C15 | C | 0.00687 | 0.14376 | 0.14619 |
| C16 | C | 0.01319 | 0.36320 | 0.36037 |
| C17 | C | 0.00310 | 0.83234 | 0.14079 |
| C18 | C | −0.00092 | 0.61721 | 0.35785 |
| C19 | C | 0.00630 | 0.14809 | 0.83547 |
| C20 | C | 0.02980 | 0.36570 | 0.61557 |
| C21 | C | 0.01008 | 0.83716 | 0.83085 |
| C22 | C | 0.02209 | 0.62158 | 0.61210 |
| C23 | C | 0.15879 | −0.00888 | 0.14587 |
| C24 | C | 0.37853 | −0.00402 | 0.36005 |
| C25 | C | 0.16202 | −0.00898 | 0.83474 |
| C26 | C | 0.38029 | 0.01030 | 0.61538 |
| C27 | C | 0.84750 | −0.01236 | 0.14144 |
| C28 | C | 0.63251 | −0.02146 | 0.35862 |
| C29 | C | 0.85141 | −0.00636 | 0.83138 |
| C30 | C | 0.63593 | −0.00013 | 0.61275 |
| C31 | C | 0.16069 | 0.14611 | −0.01027 |
| C32 | C | 0.37967 | 0.36484 | 0.01060 |
| C33 | C | 0.85001 | 0.14635 | −0.00802 |
| C34 | C | 0.63551 | 0.36567 | 0.00004 |
| C35 | C | 0.16114 | 0.83546 | −0.00984 |
| C36 | C | 0.38016 | 0.62034 | −0.00454 |
| C37 | C | 0.84961 | 0.83609 | −0.01644 |
| C38 | C | 0.63413 | 0.61967 | −0.02374 |
| C39 | C | 0.05049 | 0.25851 | 0.19383 |
| C40 | C | 0.00959 | 0.19884 | 0.20186 |
| C41 | C | 0.05340 | 0.30997 | 0.24544 |
| O42 | O | 0.00997 | 0.16404 | 0.08262 |
| C43 | C | −0.01526 | 0.45276 | 0.27282 |
| C44 | C | −0.00012 | 0.43270 | 0.33971 |
| C45 | C | 0.04842 | 0.67052 | 0.24719 |
| C46 | C | 0.04870 | 0.72096 | 0.19444 |
| C47 | C | −0.00097 | 0.67171 | 0.30079 |
| O48 | O | 0.00646 | 0.81371 | 0.07675 |
| C49 | C | −0.01764 | 0.52364 | 0.27195 |
| C50 | C | −0.00488 | 0.54630 | 0.33849 |
| C51 | C | 0.00534 | 0.27440 | 0.79622 |
| C52 | C | 0.00688 | 0.20370 | 0.78009 |
| C53 | C | 0.00769 | 0.32548 | 0.74408 |
| O54 | O | 0.00463 | 0.16701 | 0.89957 |
| C55 | C | 0.06487 | 0.46145 | 0.69565 |
| C56 | C | 0.03840 | 0.43739 | 0.63372 |
| C57 | C | −0.02082 | 0.71851 | 0.78223 |
| C58 | C | 0.01400 | 0.78205 | 0.77523 |
| C59 | C | −0.01887 | 0.66798 | 0.72957 |
| O60 | O | 0.00624 | 0.81674 | 0.89432 |
| C61 | C | 0.06050 | 0.53219 | 0.69529 |
| C62 | C | 0.03480 | 0.55154 | 0.63173 |
| C63 | C | 0.20814 | −0.04516 | 0.26306 |
| C64 | C | 0.21401 | −0.00676 | 0.20150 |
| C65 | C | 0.26114 | −0.04477 | 0.31336 |
| O66 | O | 0.09480 | −0.01364 | 0.16472 |
| C67 | C | 0.29293 | 0.03646 | 0.45110 |
| C68 | C | 0.36022 | 0.01059 | 0.42988 |
| C69 | C | 0.20096 | −0.01242 | 0.70880 |
| C70 | C | 0.21757 | −0.00972 | 0.77934 |
| C71 | C | 0.25257 | −0.01150 | 0.65737 |
| O72 | O | 0.09838 | −0.00667 | 0.81476 |
| C73 | C | 0.29423 | 0.04313 | 0.51877 |
| C74 | C | 0.36081 | 0.01747 | 0.54403 |
| C75 | C | 0.79113 | −0.06722 | 0.24652 |
| C76 | C | 0.79161 | −0.01507 | 0.19595 |
| C77 | C | 0.73898 | −0.07085 | 0.29720 |
| O78 | O | 0.91096 | −0.01550 | 0.16188 |
| C79 | C | 0.72636 | −0.02309 | 0.45162 |
| C80 | C | 0.65437 | −0.01953 | 0.42900 |
| C81 | C | 0.80296 | 0.03857 | 0.71707 |
| C82 | C | 0.79638 | −0.00430 | 0.77554 |
| C83 | C | 0.75080 | 0.04168 | 0.66599 |
| O84 | O | 0.91546 | −0.00374 | 0.81259 |
| C85 | C | 0.72687 | −0.02170 | 0.51964 |
| C86 | C | 0.65564 | −0.01302 | 0.54294 |
| C87 | C | 0.28666 | 0.18478 | −0.01117 |
| C88 | C | 0.21617 | 0.20148 | −0.01028 |
| C89 | C | 0.33813 | 0.23644 | −0.00968 |
| O90 | O | 0.18026 | 0.08226 | −0.01021 |
| C91 | C | 0.47696 | 0.27970 | 0.04449 |
| C92 | C | 0.45124 | 0.34595 | 0.01845 |
| C93 | C | 0.68413 | 0.25081 | −0.04436 |
| C94 | C | 0.73458 | 0.19803 | −0.04580 |
| C95 | C | 0.69024 | 0.30840 | −0.00019 |
| O96 | O | 0.83038 | 0.08276 | −0.01405 |
| C97 | C | 0.54468 | 0.27898 | 0.03816 |
| C98 | C | 0.56551 | 0.34651 | 0.01255 |
| C99 | C | 0.32795 | 0.73599 | 0.03563 |
| C100 | C | 0.27646 | 0.78774 | 0.03317 |
| C101 | C | 0.32355 | 0.67577 | −0.00512 |
| O102 | O | 0.18046 | 0.89929 | −0.00557 |
| C103 | C | 0.47194 | 0.71086 | −0.03349 |
| C104 | C | 0.44964 | 0.64019 | −0.01890 |
| C105 | C | 0.69027 | 0.72677 | 0.02904 |
| C106 | C | 0.74111 | 0.77897 | 0.03054 |
| C107 | C | 0.68891 | 0.67645 | −0.02354 |
| O108 | O | 0.83005 | 0.89975 | −0.01215 |
| C109 | C | 0.54000 | 0.71090 | −0.03655 |
| C110 | C | 0.56343 | 0.64003 | −0.02543 |
| C111 | C | 0.33937 | −0.01130 | 0.74377 |
| C112 | C | 0.28813 | −0.01221 | 0.79572 |
| C113 | C | 0.32373 | −0.00157 | 0.67258 |
| O114 | O | 0.18111 | −0.01032 | 0.89882 |
| C115 | C | 0.47622 | 0.04319 | 0.69617 |
| C116 | C | 0.45197 | 0.01791 | 0.63375 |
| C117 | C | 0.68545 | −0.04389 | 0.72753 |
| C118 | C | 0.73605 | −0.04475 | 0.78018 |
| C119 | C | 0.69155 | −0.00062 | 0.66923 |
| O120 | O | 0.83114 | −0.01009 | 0.89492 |
| C121 | C | 0.54686 | 0.03755 | 0.69628 |
| C122 | C | 0.56602 | 0.01281 | 0.63235 |
| C123 | C | 0.32548 | 0.03628 | 0.24495 |
| C124 | C | 0.27392 | 0.03378 | 0.19349 |
| C125 | C | 0.32113 | −0.00410 | 0.30543 |
| O126 | O | 0.17894 | −0.00534 | 0.08227 |
| C127 | C | 0.46836 | −0.03218 | 0.27257 |
| C128 | C | 0.44807 | −0.01757 | 0.33951 |
| C129 | C | 0.68753 | 0.03218 | 0.25106 |
| C130 | C | 0.73798 | 0.03396 | 0.19836 |
| C131 | C | 0.68714 | −0.02018 | 0.30174 |
| O132 | O | 0.82870 | −0.00755 | 0.07757 |

-continued

| | | | | |
|---|---|---|---|---|
| C133 | C | 0.53924 | −0.03525 | 0.27198 |
| C134 | C | 0.56164 | −0.02374 | 0.33880 |
| C135 | C | 0.00735 | 0.23828 | 0.65800 |
| C136 | C | 0.00525 | 0.18690 | 0.70958 |
| C137 | C | 0.01755 | 0.30944 | 0.67299 |
| O138 | O | 0.00748 | 0.08448 | 0.81530 |
| C139 | C | 0.06172 | 0.27943 | 0.51882 |
| C140 | C | 0.03591 | 0.34590 | 0.54416 |
| C141 | C | −0.02788 | 0.24595 | 0.31384 |
| C142 | C | −0.02858 | 0.19299 | 0.26353 |
| C143 | C | 0.01295 | 0.30577 | 0.30585 |
| O144 | O | 0.00151 | 0.07979 | 0.16493 |
| C145 | C | 0.05426 | 0.27788 | 0.45125 |
| C146 | C | 0.02780 | 0.34499 | 0.43016 |
| C147 | C | 0.05813 | 0.73936 | 0.66399 |
| C148 | C | 0.05319 | 0.79157 | 0.71474 |
| C149 | C | 0.02075 | 0.67707 | 0.66903 |
| O150 | O | 0.01092 | 0.90140 | 0.81226 |
| C151 | C | 0.00385 | 0.71270 | 0.51744 |
| C152 | C | 0.01018 | 0.64125 | 0.54188 |
| C153 | C | −0.04692 | 0.77793 | 0.24912 |
| C154 | C | 0.00165 | 0.77637 | 0.19518 |
| C155 | C | −0.04975 | 0.72552 | 0.29945 |
| O156 | O | 0.00006 | 0.89579 | 0.16142 |
| C157 | C | 0.00271 | 0.71144 | 0.44989 |
| C158 | C | 0.00343 | 0.63934 | 0.42802 |
| C159 | C | 0.25177 | 0.32324 | −0.01211 |
| C160 | C | 0.19987 | 0.27201 | −0.01352 |
| C161 | C | 0.32279 | 0.30780 | −0.00111 |
| O162 | O | 0.09681 | 0.16563 | −0.01016 |
| C163 | C | 0.29811 | 0.46072 | 0.04204 |
| C164 | C | 0.36067 | 0.43659 | 0.01699 |
| C165 | C | 0.21132 | 0.71910 | −0.04712 |
| C166 | C | 0.21681 | 0.78019 | −0.00794 |
| C167 | C | 0.26407 | 0.66861 | −0.04660 |
| O168 | O | 0.09745 | 0.81589 | −0.01537 |
| C169 | C | 0.29748 | 0.53126 | 0.03536 |
| C170 | C | 0.36116 | 0.55056 | 0.01003 |
| C171 | C | 0.80081 | 0.25921 | 0.03949 |
| C172 | C | 0.79463 | 0.20180 | −0.00486 |
| C173 | C | 0.74884 | 0.31040 | 0.04307 |
| O174 | O | 0.91386 | 0.16564 | −0.00424 |
| C175 | C | 0.72372 | 0.45676 | −0.02022 |
| C176 | C | 0.65602 | 0.43553 | −0.01205 |
| C177 | C | 0.79294 | 0.73126 | −0.07177 |
| C178 | C | 0.79414 | 0.78137 | −0.01910 |
| C179 | C | 0.74035 | 0.68082 | −0.07486 |
| O180 | O | 0.91334 | 0.81623 | −0.01880 |
| C181 | C | 0.72357 | 0.52750 | −0.02361 |
| C182 | C | 0.65551 | 0.54909 | −0.02085 |
| N183 | N | 0.00310 | 0.49021 | 0.37972 |
| N184 | N | 0.02529 | 0.49346 | 0.59334 |
| N185 | N | 0.40020 | 1.00443 | 0.48733 |
| N186 | N | 0.61417 | 0.98603 | 0.48627 |
| N187 | N | 0.50775 | 0.38587 | 1.00565 |
| N188 | N | 0.50680 | 0.59952 | 0.98286 |
| N189 | N | 0.50808 | 1.00489 | 0.59347 |
| N190 | N | 0.50547 | 0.98486 | 0.37982 |
| N191 | N | 0.02136 | 0.38495 | 0.48755 |
| N192 | N | 0.00789 | 0.59924 | 0.48547 |
| N193 | N | 0.40049 | 0.49280 | 1.00275 |
| N194 | N | 0.61474 | 0.49232 | 0.98584 |
| H195 | H | 0.08142 | 0.26465 | 0.14772 |
| H196 | H | 0.08713 | 0.35378 | 0.23782 |
| H197 | H | −0.02386 | 0.42002 | 0.22860 |
| H198 | H | 0.08715 | 0.63036 | 0.24638 |
| H199 | H | 0.08707 | 0.71792 | 0.15400 |
| H200 | H | −0.02855 | 0.55490 | 0.22712 |
| H201 | H | 0.00075 | 0.29041 | 0.84955 |
| H202 | H | −0.00241 | 0.37724 | 0.76096 |
| H203 | H | 0.09048 | 0.43197 | 0.73532 |
| H204 | H | −0.05115 | 0.70870 | 0.82794 |
| H205 | H | −0.04897 | 0.62148 | 0.73571 |
| H206 | H | 0.07851 | 0.56597 | 0.73581 |
| H207 | H | 0.16282 | −0.07676 | 0.27162 |
| H208 | H | 0.25525 | −0.07661 | 0.35886 |
| H209 | H | 0.25154 | 0.05393 | 0.41803 |
| H210 | H | 0.14753 | −0.01751 | 0.69313 |
| H211 | H | 0.23500 | −0.02345 | 0.60625 |
| H212 | H | 0.25488 | 0.06983 | 0.54781 |
| H213 | H | 0.83087 | −0.10597 | 0.24619 |
| H214 | H | 0.73973 | −0.11300 | 0.33380 |
| H215 | H | 0.77211 | −0.02754 | 0.42025 |
| H216 | H | 0.84840 | 0.07058 | 0.71140 |
| H217 | H | 0.75722 | 0.07681 | 0.62312 |
| H218 | H | 0.77283 | −0.02669 | 0.55074 |
| H219 | H | 0.30227 | 0.13128 | −0.01498 |
| H220 | H | 0.38942 | 0.21870 | −0.02012 |
| H221 | H | 0.44823 | 0.24056 | 0.07186 |
| H222 | H | 0.64000 | 0.24685 | −0.07830 |
| H223 | H | 0.72751 | 0.15471 | −0.08035 |
| H224 | H | 0.57805 | 0.23820 | 0.05642 |
| H225 | H | 0.37178 | 0.74328 | 0.06938 |
| H226 | H | 0.28254 | 0.83358 | 0.06452 |
| H227 | H | 0.43993 | 0.75560 | −0.04220 |
| H228 | H | 0.65164 | 0.72556 | 0.06929 |
| H229 | H | 0.73995 | 0.81688 | 0.07155 |
| H230 | H | 0.57135 | 0.75557 | −0.04793 |
| H231 | H | 0.39070 | −0.02281 | 0.76101 |
| H232 | H | 0.30380 | −0.01696 | 0.84913 |
| H233 | H | 0.44702 | 0.06869 | 0.73615 |
| H234 | H | 0.64116 | −0.07757 | 0.73211 |
| H235 | H | 0.72893 | −0.07859 | 0.82407 |
| H236 | H | 0.58063 | 0.05385 | 0.73756 |
| H237 | H | 0.36959 | 0.06944 | 0.23684 |
| H238 | H | 0.28034 | 0.06471 | 0.14748 |
| H239 | H | 0.43565 | −0.04006 | 0.22821 |
| H240 | H | 0.64838 | 0.07192 | 0.25236 |
| H241 | H | 0.73609 | 0.07469 | 0.16020 |
| H242 | H | 0.57069 | −0.04611 | 0.22725 |
| H243 | H | −0.00338 | 0.22047 | 0.60679 |
| H244 | H | 0.00072 | 0.13343 | 0.69394 |
| H245 | H | 0.08941 | 0.24061 | 0.54768 |
| H246 | H | −0.05948 | 0.24013 | 0.35946 |
| H247 | H | −0.06011 | 0.14768 | 0.27218 |
| H248 | H | 0.07217 | 0.23680 | 0.41806 |
| H249 | H | 0.08868 | 0.74919 | 0.61833 |
| H250 | H | 0.08010 | 0.83966 | 0.70616 |
| H251 | H | 0.00256 | 0.76052 | 0.54572 |
| H252 | H | −0.08308 | 0.81984 | 0.25215 |
| H253 | H | −0.08921 | 0.72807 | 0.33880 |
| H254 | H | 0.00190 | 0.75750 | 0.41899 |
| H255 | H | 0.23459 | 0.37449 | −0.02411 |
| H256 | H | 0.14660 | 0.28782 | −0.01912 |
| H257 | H | 0.25825 | 0.43152 | 0.06774 |
| H258 | H | 0.16650 | 0.71116 | −0.07953 |
| H259 | H | 0.25838 | 0.62351 | −0.07898 |
| H260 | H | 0.25584 | 0.56482 | 0.05115 |
| H261 | H | 0.84578 | 0.26389 | 0.07235 |
| H262 | H | 0.75496 | 0.35248 | 0.07921 |
| H263 | H | 0.76949 | 0.42521 | −0.02274 |
| H264 | H | 0.83225 | 0.73199 | −0.11143 |
| H265 | H | 0.74034 | 0.64432 | −0.11708 |
| H266 | H | 0.76936 | 0.55886 | −0.02743 |
| Mo267 | Mo | 0.50696 | 0.99461 | 0.48679 |
| O268 | O | 0.49872 | 0.90289 | 0.49590 |
| Mo269 | Mo | 0.50742 | 0.49260 | 0.99374 |
| O270 | O | 0.49994 | 0.48261 | 0.90196 |
| Mo271 | Mo | 0.01338 | 0.49206 | 0.48667 |
| O272 | O | 0.10539 | 0.49706 | 0.47652 |

What is claimed is:

1. A photoresponsive oxygen storage material comprising:
a plurality of unit cells,
wherein each of the plurality of unit cells has a shape of a cube having eight corners and six faces,
each of the plurality of unit cells includes
a plurality of zirconium-oxo clusters each located at a corresponding corner of the eight corners, and
a plurality of ligands each located on a corresponding face of the six faces and each having a porphyrin skeleton and including greater than or equal to 1 and less than or equal to 4 carboxy groups,
a molybdenum ion is located at a center of the porphyrin skeleton, and
at least some of the plurality of unit cells are empty.

2. The photoresponsive oxygen storage material according to claim 1,
wherein the molybdenum ion is an oxomolybdenum ion.

3. The photoresponsive oxygen storage material according to claim 1,
wherein the plurality of zirconium-oxo clusters are each represented by $Zr_6(OH)_4O_4$.

4. The photoresponsive oxygen storage material according to claim 1,
wherein the plurality of ligands are each a porphyrin including 4 carboxy groups.

5. An oxygen storage apparatus comprising:
a container; and
the photoresponsive oxygen storage material according to claim 1, the photoresponsive oxygen storage material being disposed in the container.

6. A method for storing oxygen molecules, comprising:
bringing the photoresponsive oxygen storage material according to claim 1 into contact with gas containing the oxygen molecules to store the oxygen molecules inside the photoresponsive oxygen storage material.

7. The method according to claim 6,
wherein the molybdenum ion is an oxomolybdenum ion.

8. The method according to claim 6,
wherein the plurality of zirconium-oxo clusters are each represented by $Zr_6(OH)_4O_4$.

9. The method according to claim 6,
wherein the plurality of ligands are each a porphyrin including 4 carboxy groups.

10. A method for releasing oxygen molecules from the photoresponsive oxygen storage material of claim 1, the method comprising:
irradiating the photoresponsive oxygen storage material with light to release oxygen molecules from the photoresponsive oxygen storage material,
wherein the oxygen molecules are stored inside at least some of the plurality of unit cells.

11. The method according to claim 10,
wherein the molybdenum ion is an oxomolybdenum ion.

12. The method according to claim 10,
wherein the plurality of zirconium-oxo clusters are each represented by $Zr_6(OH)_4O_4$.

13. The method according to claim 10,
wherein the plurality of ligands are each a porphyrin including 4 carboxy groups.

14. The photoresponsive oxygen storage material according to claim 1,
wherein the porphyrin skeleton has a structure as shown below and M is the molybdenum ion

* * * * *